United States Patent [19]
Reilly et al.

[11] 3,965,902
[45] June 29, 1976

[54] DISPOSABLE FLUID COLLECTION CONTAINER

[75] Inventors: Richard J. Reilly, Deerfield; Walter Goza Cornett, III, Wilmette, both of Ill.; James H. Riddle, Indianapolis; David Wharmby, Noblesville, both of Ind.

[73] Assignee: Respiratory Care, Inc., Arlington Heights, Ill.

[22] Filed: Oct. 17, 1974

[21] Appl. No.: 515,619

Related U.S. Application Data
[63] Continuation of Ser. No. 344,412, March 23, 1973, abandoned.

[52] U.S. Cl. .................................. 128/276; 141/59
[51] Int. Cl.² .......................................... A61M 1/00
[58] Field of Search ................... 128/275, 276, 277; 137/199, 205, 433; 141/4, 5, 7, 8, 39–42, 46, 59, 61, 65, 66, 100, 198, 286, 303, 325–327; 222/543

[56] References Cited
UNITED STATES PATENTS

| | | | |
|---|---|---|---|
| 2,495,905 | 1/1950 | Pogue | 141/59 X |
| 3,485,404 | 12/1969 | Newton | 128/276 X |
| 3,685,517 | 8/1972 | Reynolds | 141/61 X |
| 3,699,815 | 10/1972 | Holbrook | 128/276 X |

*Primary Examiner*—Richard E. Aegerter
*Assistant Examiner*—Frederick R. Schmidt
*Attorney, Agent, or Firm*—Eric P. Schellin

[57] ABSTRACT

There is disclosed a suction operated body fluid collection bottle having cylindrical portion terminating in a dome-shaped portion. An opening is positioned centrally with respect to said dome. The sides of the opening are arranged to accept a screw cap closure. The said closure has an upwardly standing nipple arranged to be attached to a suction conduit line and a second nipple arranged to be attached to a conduit terminating at the other end at a source of body fluids. The arrangement of the bottle is designed to aspirate the body fluids into the container without permitting the fluids to actually reach the suction line. In another embodiment the aperture has an insert container which extends downwardly into the container. The insert container is calibrated to receive accurately measurable, small quantities of body fluid collected within both the bottle and the insert. Such insert includes overflow means whereby quantities in excess of a predetermined amount can overflow into the interior of the bottle.

3 Claims, 8 Drawing Figures

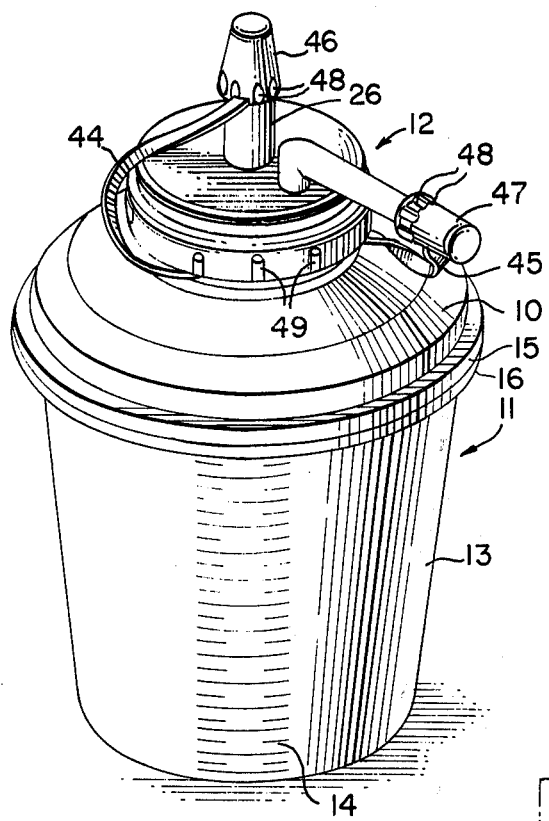
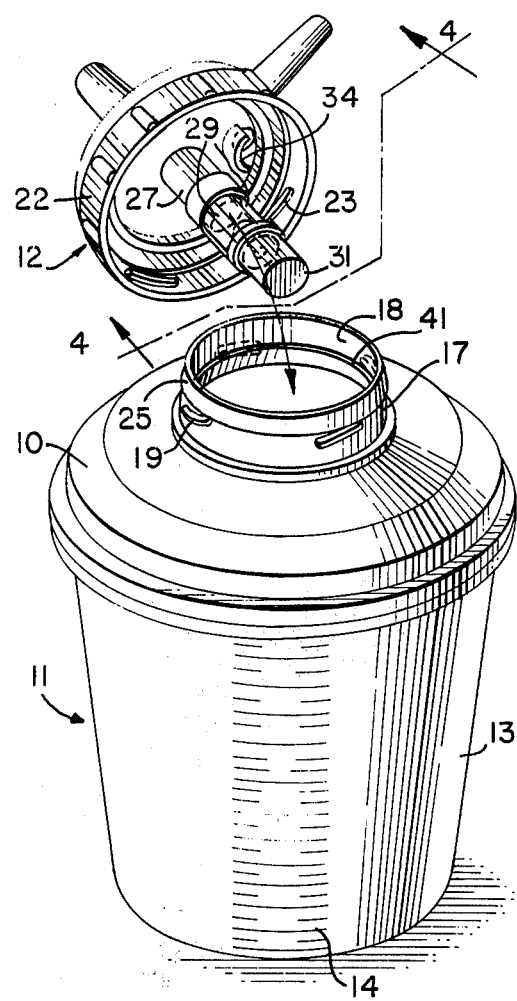
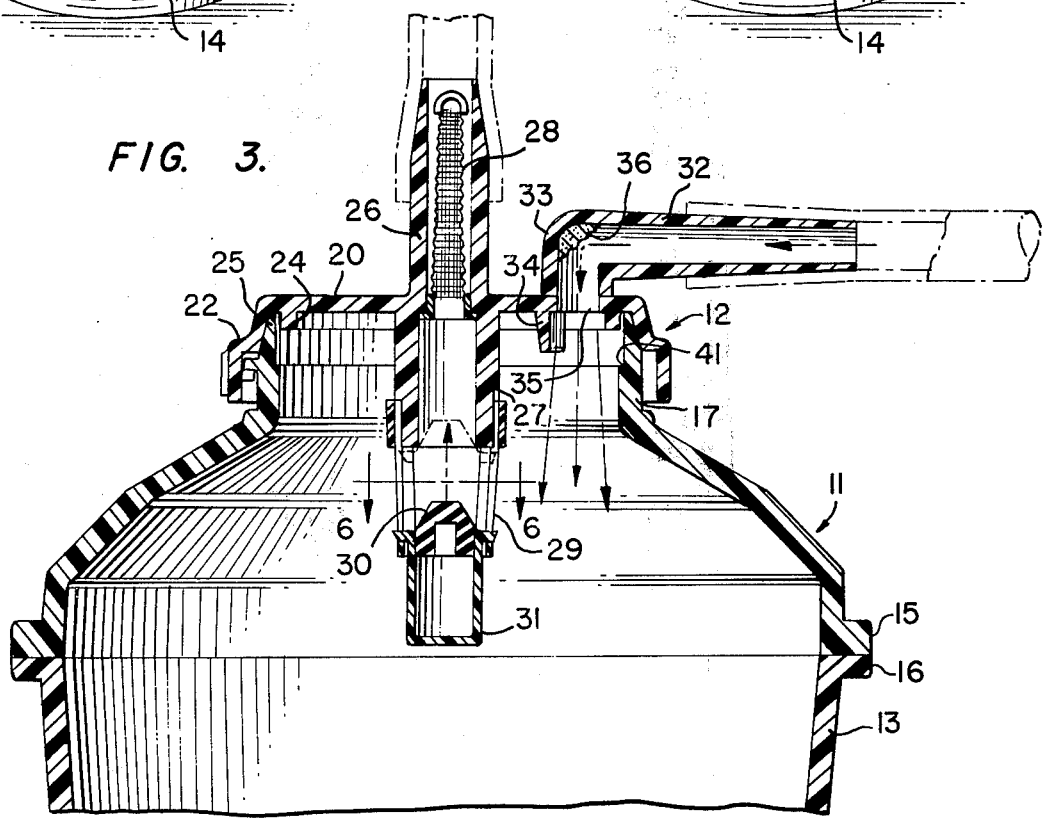

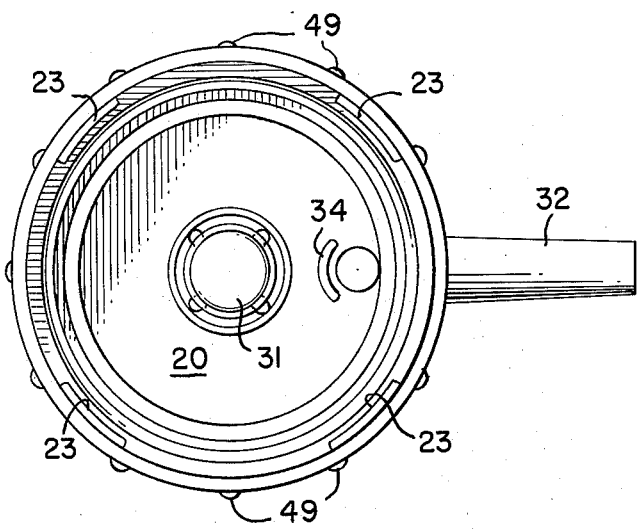
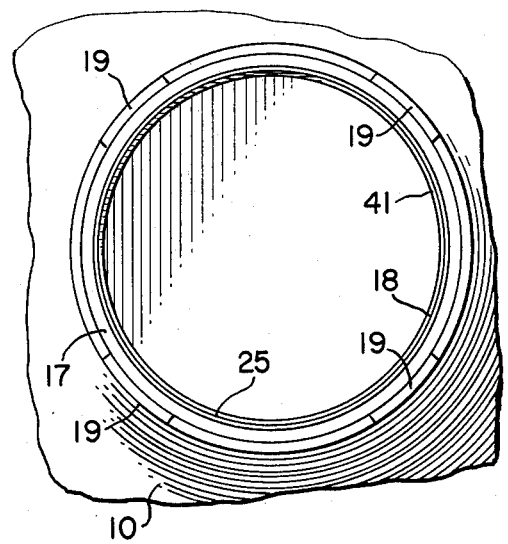
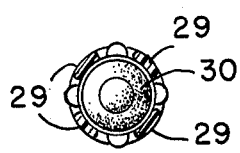
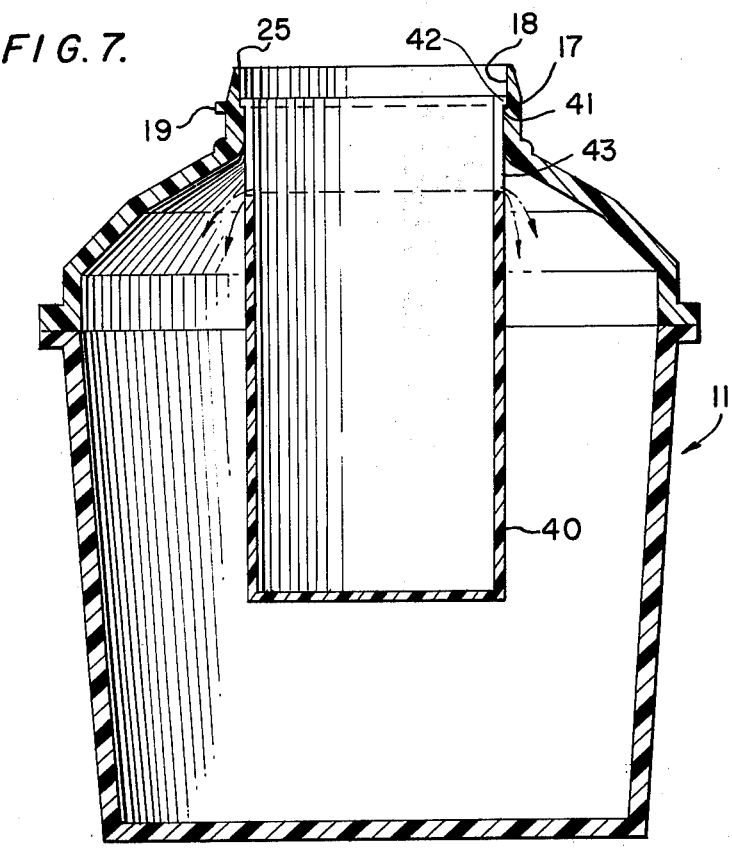
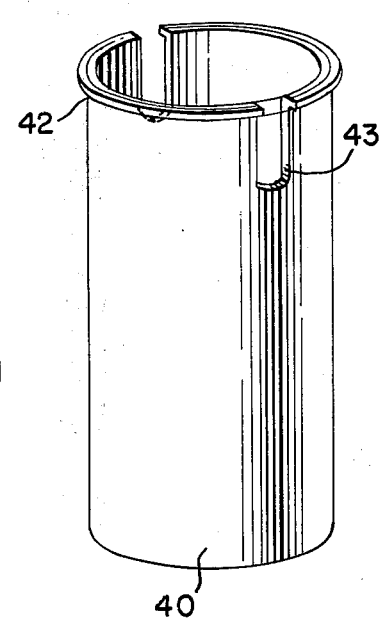

DISPOSABLE FLUID COLLECTION CONTAINER

This is a continuation of application Ser. No. 344,412 filed Mar. 23, 1973, now abandoned.

BACKGROUND OF THE INVENTION

Vacuum operated bottles are being used in hospitals and the like. These bottles are employed for collecting body fluid such as blood from a patient during or after surgery. The bottle construction of the devices of the prior art have appeared commercially in a limited number of designs. For the most part such bottles have been constructed of glass having at the most only disposable lids. These lids have port means of some type designed to accept one end of a suction tube. The lid also possesses another port means to which the terminal portion of another tube is matingly secured. The other end of the tube is positioned at the site of the body fluid to be aspirated.

It will be appreciated that as such prior containers were not designed to be disposed after a single use, due to the rather high expense of such containers, the task of emptying such containers is an unpleasant task. These containers are rather large usually containing up to two liters of fluid. Handling this much fluid in a container which must be carefully opened to avoid spillage can lead to problems. First of all, as the containers must be subjected to negative pressure the lids must be tightly sealed which results in a tight fit on the part of the lid which must be defeated when it is to be opened.

As will be illustrated and demonstrated, the collection container of the present invention is arranged and constructed to avoid some of the difficulties of the prior art especially the need for emptying liquid filled containers as the container of the present invention by being a rather inexpensive item may be discarded after only a single use without emptying the liquid contents therefrom.

SUMMARY OF THE INVENTION

The invention relates to a container consisting of a domed bottle with a centrally located aperture at the end of a short neck. A screw closure is designed to close the aperture. The closure has two nipples at the end of conduits which communicate with the inside of the bottle. One nipple is designed to be connected to a source of a vacuum through a suitable conduit. This nipple has a filter positioned therein and a valve means to effectively prevent any of the liquid collected in the bottle from passing through the conduit into the vacuum line. The other nipple is designed to have a conduit affixed thereto for communication with a source of body fluid which is to be collected in the bottle in measurable quantities. Means is provided in the latter nipple for introducing a small quantity of an antifoaming material.

The entire container is easily assembled from thermoplastic molded parts so that the entire container including the contents may be discarded.

As the container of the present invention is of a relatively large size, it has been found propitious to sealingly mount a small insert receptacle within the confines of the neck and extend such insert receptacle into the bottle. The insert receptacle is permitted to be filled first and then any additional quantity is spilled into the bottle.

BRIEF DESCRIPTION OF THE DRAWINGS

For a full and more complete understanding of the invention, reference may be had to the following description and the accompanying drawing wherein:

FIG. 1 is a perspective view of the bottle of the present invention with the closure secured to the bottle.

FIG. 2 is a similar perspective view with the closure exploded therefrom and turned about 90° to reveal the underside of the closure.

FIG. 3 is a cross-sectional view of a fragmentary portion of the bottle and the closure in a secured position.

FIG. 4 is a bottom view of the closure.

FIG. 5 is a fragmentary top view of the bottle showing the aperture of the bottle.

FIG. 6 is a cross-sectional view taken along line 6—6 of FIG. 3.

FIG. 7 is a cross-sectional view of the entire bottle and of an insert in another embodiment of the invention.

FIG. 8 is a perspective view of the insert as it would appear prior to be permanently affixed in the position shown in FIG. 7.

DETAILED CONSIDERATION OF THE INVENTION

The bottle of the present invention is generally shown by reference numeral 11. The closure which is threadingly engaged onto the bottle is designated generally by reference numeral 12.

The bottle has a main cylindrical cup-like portion 13 with graduations 14 along one side. The cup-like portion 13 is enclosed at the top opening with a dome 10. Both the top of the cup-like portion and the outer lowermost peripheral portion of the dome possess radial flanges 15 and 16, respectively. These flanges are complementary and are sealed together as with a glue or sonic welding, for instance.

The dome has centrally located cylindrical neck 17 which terminates in an opening 18 as can be seen in FIGS. 2 and 5. The neck 17 along the outer periphery has a plurality of inclined lugs 19 which are positioned to provide interrupted spaced screw threads. The closure 12 has a top wall 20 with a downwardly descending skirt 22. The inner periphery of the skirt has a series of lugs 23 which are arranged to provide interrupted spaced screw threads which threadingly engage the lugs 19 on the neck 17. More will be stated with regard to the additional utility of the cooperation of the lugs 19 and 23.

The underside of the top wall 20 has a second smaller annular downwardly depending skirt 24 spaced inwardly from skirt 22. The upwardly extending face 25 and the immediate portion therebelow of the neck 17 is arranged and constructed to fit relatively snugly between the space described between the skirt 22 and 24 to provide a good seal. The top wall 20 also has located centrally an upwardly extending nipple 26. In communication with the nipple 26 but depending therefrom is a relatively short conduit 27. Nipple 26 and conduit 27 together provide a bore for communicating the inside of the bottle 11 with the outside. The nipple 26 is fitted with a conical elongated screen 28 which acts as a filter.

At the bottom portion of the conduit 27 is a downwardly depending cage 29 in which is positioned a bouyant valve 30 which seats against the opening of conduit 27. The valve 30 has a float portion 31. The valve is able to float on the surface of a liquid when present at a level within the dome. Under those circumstances where the liquid level actually reaches close to the end of conduit 27, the valve will float upwardly to become seated against the opening of conduit 27. Under normal situations with the bottle in an upright position the valve will be urged downwardly due to normal gravity.

The top wall 20 has a second nipple 32 which is connected to the top wall by a right angle elbow 33. The underside of top wall 20 has a small arcuate baffle 34 between the opening 35 and the conduit 27. Within the elbow 33 is a relatively small quantity of an antifoaming material 36 so that liquid flowing through nipple 32 has a small quantity of the antifoaming material introduced in the liquid stream prior to entrance of the liquid into the bottle.

Applicable antifoaming materials are well known such as the methylsiloxane polymers containing small amounts of fine particle size silica fillers such as fume silica or slica aerogel. These antifoaming agents are subject of a number of U.S. Patents such as U.S. Pat. Nos. 3,015,645; 3,024,126 and 3,304,266. Also U.S. Pat. No. 3,200,080 is applicable in providing a good exposition on the use of antifoaming agents in a flowing stream.

Attention is now directed to FIGS. 7 and 8 for a review of another embodiment of the present invention. It will be noted that bottle 11 has an insert container 40 suspended and positioned centrally with respect to the bottle. As the neck 17 is provided internally with a shoulder 41 and the insert container 40 has a radial flange 42, the insert container 40 is suspended by the flange on the shoulder 41. It is secured in that position by glue or sonic welding, for instance. The insert container has slots 43 to permit communciation between the inside of the insert container and the zone outside which, of course, is inside bottle 11.

Turning to FIG. 1 it will be seen therefrom that the closure 12 has secured to the skirt 22 an end of each of two tethers 44 and 45. The tether 44 has attached to it at the other end a cap 46 which is adapted to fit snugly by friction fit onto the mouth of nipple 26 to thereby close the nipple. Likewise, the tether 45 has attached to it at the other end a cap 47 which is arranged and constructed to fit snugly by friction fit onto the mouth of nipple 32 to thereby close that nipple. Each of the caps 46 and 47 have a plurality of raised knurls 48 outside of the caps to provide a better finger grip while affixing or removing the caps. Externally with respect to the skirt 22 are a plurality of spaced axial projections 49 also designed to provide a better hand grip when the closure 12 is to be screwed on or off the bottle 11.

In operation the container presented prior to use is in the manner shown essentially by FIG. 1. Caps 46 and 47 are removed. A suction conduit is attached to nipple 26 and another conduit is attached to nipple 32, the other end of which terminates at the source of the fluid to be aspirated. The fluid enters the container in the direction of the arrows shown in FIG. 3. Baffle 34 is useful in preventing the fluid from hitting conduit 27 and the valve 30 from which it would be possible to aspirate some undesired fluid into the suction line. As the fluid enters it picks up a small quantity of the antifoaming material in the right angle elbow 33 carrying it down into the container thereby inhibiting foam therein.

The container of the present invention is constructed of transparent thermoplastic material so that the liquid contents therein may be viewed. As the container is calibrated with graduations the quantity of the liquid collected may be determined.

When the container has been appropriately filled to a desired level the suction conduit is disengaged as well as the fluid collecting conduit. The nipples are recapped and the entire container with the contents therein may be discarded.

In the embodiment exemplified by FIG. 7, that is, showing a bottle having the insert receptacle 40, the bottle is used in the same manner. The liquid instead of going directly into the bottle enters the insert receptacle until it is filled up to openings 43 from which the liquid spills out into the bottle. The insert receptacle is also calibrated with graduations so that the quality accumulated may be discerned. The bottle of the present invention is employed when the container is to be used in conjunction with pediatric patients.

While the closure 12 has been arranged and constructed to be screwed onto the neck of the bottle, the lugs are adapted to cooperate in a manner so that the closure need not be securely screwed down. Even if the closure is only loosely in place, the application of vacuum to the inside of the bottle will operate to further rotate and screw down the closure without further manual assistance.

The parts of the present invention are all constructed of thermoplastic inexpensive materials. The closure including the tethers 44 and 45 and caps 46 and 47 are integrally molded so that the tethers have thin elongated strip configurations.

What is claimed is:

1. A transparent completely disposable, vacuum-operated, body fluid collection container adaptable for single use particularly in pediatric as well as general surgical use, and disposable without need for emptying the liquid contents thereof, said disposable container comprising the combination of
   a. transparent peripherally walled container body member having a transverse bottom wall, a generally dome-like top wall extending upwardly above a top portion of the transparent peripheral body wall and terminating in an upwardly extending annular neck portion centrally of the container body member;
   b. said neck portion defining an aperture providing communication with the inside of said container;
   c. a selectively removable closure member for normally closing said neck portion aperture, said closure member having an upwardly extending first nipple means communicating with a downwardly extending open-ended conduit means for collectively providing a part of said communication with the inside of said container, said first nipple means adaptable for connection with a vacuum source when in use;
   d. said first nipple conduit means having its open end terminating generally above and not below the top portion of the peripheral body wall so as to be within said dome-like top wall, and having longitudinal, open cage-forming means at said open end with an axially movable float valve operatively retained the rein and adaptable to close off said open end conduit means responsive to a liquid being collected therein reaching the level of said float valve to actuate same;

e. said closure member also having a right-angle elbow conduit means spaced from said first nipple means and conduit and terminating at one end exteriorly of said container in a second nipple extending laterally in a direction away from said first nipple means, and having the other end terminating in a partially peripherally baffled opening within said closure adjacent to and partially baffled longitudinally to protectively shield said float valve and open end of said first nipple conduit means from incoming collected body fluid;

f. said second nipple means together with said elbow conduit means adaptable to provide communication access for body fluid being collected in said disposable container via a conduit connectable with said second nipple means, with said elbow conduit means adapted to retard fluid flow to reduce splash, said right angle elbow conduit including internally a deposit of anti-foaming means for introduction and mixture with said body fluid being collected prior to entrance of said fluid into said container;

g. nipple-closing removable cap means including integrally connected nipple caps and tethers connected with said container closure member;

h. complemental coacting labyrinth type sealing means and inclined thread-like lug means on said container neck portion and on downwardly depending annular skirt-like wall means on said closure member, said coacting lugs constructed and arranged to provide screw-like attachment of the closure member to said container body; and i. wherein said labyrinth type sealing means and the relative relationship of said thread-like lugs of said closure member and neck are such as to provide both initial manual at least partial assembly of the closure member with the container neck portion, and also subsequent automatic continued assembly responsive to the pull of a vacuum source connected with said first nipple means.

2. A disposable body fluid collection container as defined in claim 1, further including filter means positioned within at least said first nipple means; and calibrated indicia means on said peripheral wall.

3. A disposable body fluid collection container as defined in claim 1 wherein the said neck has internally an upwardly facing shoulder, said container further including an insert receptacle extending downwardly into said container having a diameter smaller than said aperture, said insert receptacle having a radial flange adapted to be affixed to said shoulder, said shoulder and said flange adapted to suspend said insert receptacle within said container, and said insert receptacle has at least one opening at the top portion thereof to provide access from the inside of the container to the inside of the insert receptacle.

* * * * *